(12) United States Patent
Meyer et al.

(10) Patent No.: US 6,916,947 B2
(45) Date of Patent: Jul. 12, 2005

(54) METHOD OF PRODUCING AMINO CARBOXYLIC ACIDS

(75) Inventors: Oliver Meyer, Münster (DE); Thomas Kalz, Herne (DE); Karlheinz Drauz, Freigericht (DE)

(73) Assignee: Degussa AG, Dusseldorf (DE)

( * ) Notice: Subject to any disclaimer, the term of this patent is extended or adjusted under 35 U.S.C. 154(b) by 59 days.

(21) Appl. No.: 10/303,078

(22) Filed: Nov. 25, 2002

(65) Prior Publication Data

US 2003/0120084 A1 Jun. 26, 2003

(30) Foreign Application Priority Data

Nov. 29, 2001 (DE) ............................. 101 58 537

(51) Int. Cl.⁷ ............................................. C07C 229/00
(52) U.S. Cl. ....................................... 560/155; 560/171
(58) Field of Search ................................. 560/155, 171, 560/157

(56) References Cited

U.S. PATENT DOCUMENTS 4,147,716 A * 4/1979 Chung ........................ 558/394
4,234,744 A   11/1980 Effenberger et al. ........ 562/562

FOREIGN PATENT DOCUMENTS

| DE | 28 54 627 | 12/1978 | ......... C07C/101/04 |
| FR | 1.346.045 | 11/1963 | |
| WO | WO 98/50341 | 11/1998 | ......... C07C/229/00 |

OTHER PUBLICATIONS

Bell, et al., "Synthesis, C–13 NMR, and X–Ray Crystal Structure of N6, N9–Octamethylenepurinecyclophane," *Can. J. Chem.* 70:186–196 (1992).

Chiusoli, "Neuere Synthesen mit Kohlenmonoxyd," *Angewandte Chemie* 72:74–79 (1960).

Effenberger, et al., "Darstellung von Aminosäuren aus Halogencarbonsäure–alkyl–estern mit Alkalimetallcyanaten," *Chem. Ber.* 114:173–189 (1981).

Ghiaci, et al., "A Facile Beckmann Rearrangement of Oximes with AlCl₃ in the Solid State," *Synth. Comm.* 28:2275–2280 (1998).

Ho, et al., "A Practical Synthesis of ω–Aminoalkanoic Acid Derivatives from Cycloalkanones," *Synth. Comm.* 26:2641–2649 (1996).

Khodaei, et al., "Solvent Free Beckmann Rearrangement of Ketoximes by Anhydrous Ferric Chloride," *Synth. Comm.* 31:2047–2050 (2001).

Laurent, e al., "Fast Synthesis of Amino Acid Salts and Lactams without Solvent under Microwave Irradiation," *J. Chem. Soc., Chem. Commun.* 11:1101 (1995).

Olah, et al., "Synthesis Methods and Reactions; One–Step Conversion of Alicyclic Ketones into Lactams with Hydroxylamine–O–Sulfonic Acid/Formic Acid," *Synthesis* 537–538 (1979).

Robinson, et al., "Synthesis of Certain Higher Aliphatic Compounds. Part II. The Hydration of Stearolic Acid," *J. Chem. Soc.* 2204–2209 (1926).

Rondel, et al., "The Mechanism of the Action of Fused Alkalis. Part I. The Action of Fused Potassium Hydroxide on Dihydroxystearic Acid and Dihydroxybehenic Acid," *J. Chem. Soc.* 2800–2819 (1914).

Takagi, et al., "Studies on the Synthesis of Amino Acids by the Schmidt Reaction. II. New Synthetic Method for ω–Amino Acids and Syntheses of DL–2,8–Diaminoöctanoic Acid and DL–2,9–Diaminononanoic Acid," *Chem. Pharm. Bull.* 7:99–102 (1959).

Treibs, et al., "Synthesen mit Dicarbonsäuren, XIX. Mitteil. Darstellung von ω–Aminocarbonsäuren durch halbseitigen Hofmannshchen Abbau von Dicarbonsäuren," *Chem Ber.* 89:117–120 (1956).

Abstract for AH1 above.

Effenberger, et al., "Neue Synthese von Aminosäuren aus Halogencarbon–säureestern," *Angewandte Chemie* 91:504–505 (1979).

* cited by examiner

Primary Examiner—Paul A. Zucker
(74) Attorney, Agent, or Firm—Michael A. Sanzo; Fitch, Even, Tabin & Flannery

(57) ABSTRACT

The present invention is directed to a method for producing amino acids by reacting halogenated carboxylic acid ester (haloacid esters) with a metal cyanate in the presence of an alcohol and by subsequent acidic saponification of the urethane carbonic acid formed. The method is characterized by the metal cyanate being placed at an elevated temperature in an organic solvent and the other reactants being continuously charged into the mixture over a defined time period.

18 Claims, No Drawings

METHOD OF PRODUCING AMINO CARBOXYLIC ACIDS

CROSS REFERENCE TO RELATED APPLICATIONS

The present application claims priority to German application DE 101 58 537.3, filed on Nov. 29, 2001, the contents of which is hereby incorporated by reference.

FIELD OF THE INVENTION

The present invention is directed to a method for producing amino acids in which a halogenated carboxylic acid ester is reacted with a metal cyanate and an alcohol to form a urethane carbonic acid ester. This then undergoes a saponification reaction to release the amino acid.

BACKGROUND OF THE INVENTION

Amino acids are used in, inter alia, parenteral or animal nourishment, organic syntheses (e.g., in polymer chemistry), and as synthetic structural elements for the preparation of pharmaceutical products. Because of their importance in the area of polymer chemistry, O-amino acids have received a particularly large amount of attention and many methods for the synthesis of these compounds have appeared in the literature. For example, O-amino octanoic acid can be produced from cyclooctanone by Beckmann rearrangement with subsequent ring opening (WO 9850341; *Synth. Commun.* 31:2047–2050 (2001); *Synth. Commun.* 28:2275–2280 (1998); *Synth. Commun.* 16:2641–2649 (1996); *J. Chem. Soc., Chem. Commun.* 1101 (1995); *Synthesis* 537–538 (1979); *Can. J. Chem.* 70:86–196 (1992)). In addition, other Beckmann rearrangements can be performed starting from longer-chain, aliphatic oximes (*Chem. Ber.* 29:806–809 (1896); *Chem. Ber.* 27:3121–3129 (1894); *J. Chem. Soc.* 105:2809 (1914); *J. Chem. Soc.* 2207 (1926)). O-amino octanoic acid can also be synthesized by the unilateral Hoffmann degradation of azelaic acid (*Chem. Ber.* 89:177–120 (1956)) or by Curtis rearrangement of an azelaic acid monoalkylester (*Chem. Pharm. Bull.* 7:99–100 (1959)). Other methods described in the literature include: synthesis by hydrogenation of 7-cyanoheptanoic acid (Izv. Akad. Nauk. USSR, Ser. Khim. 224–229 (1955), Engl. edition 199–205); by hydrogenation of 7-cyano-2,5-heptadienic acid (DE 1081469; *Agnew. Chem.* 72:74–76 (1960)); by reacting 8,8-dichloro-7-octenyl amine with aqueous sulfuric acid (*Zh. Obshch. Khim.* 27:2418–2421 (1957), Engl. edition 2481–2484); and by reacting the corresponding O-chlorocarboxylic acid with liquid ammonia (FR 1346045). All of these methods either suffer from poor accessibility of reactants, have low reaction yields, or cannot practically be carried out on a large scale.

The reaction of a halogenated carboxylic acid ester with alkali metal cyanates in the presence of an alcohol and subsequent double saponification of the formed urethane carbonic acid ester to amino acid has been suggested in the literature (DE 2854627; *Agnew. Chem.* 91:504–505 (1979); *Chem. Ber.* 114:173–189 (1981)). In particular, authors report the synthesis of amino acids by the reaction of bromo- or chloro-substituted carbonic acid esters in polar aprotic solvents with alkali metal cyanate in the presence of an alcohol to form urethane. This then undergoes acidic hydrolysis. However, only the use of comparatively short-chain halogenated carboxylic acid esters, i.e., with a maximum chain length of six carbon atoms, is described. Nothing is reported concerning the synthesis of higher-chain derivatives. Moreover, the disclosed method will require substantially longer reaction times for the conversion of chlorocarboxylic acid esters to urethane than for the conversion of the corresponding bromocarboxylic acid esters. For example, 6-chlorohexanoic acid methylester requires 30 hours of reaction time for a complete conversion to 6-(methoxycarbonylamino)-hexanoic acid methylester, whereas 6-bromohexanoic acid methylester is completely converted after only 0.75 hours. Since chlorine compounds are generally preferred in large scale industrial syntheses, this is a serious drawback. In addition, the hydrolytic splitting of the urethane group using a mixture of formic acid and hydrochloric acid in water appears to require 24 hours of heating at reflux temperature. This would also make the procedure generally undesirable for large-scale use.

SUMMARY OF THE INVENTION

The present invention is concerned with a new method of producing amino carboxylic acids that is suitable for large-scale operation both from an economic and ecological standpoint. Specifically, the invention is directed to a method for producing an amino acid by reacting a halogenated carboxylic acid ester with a metal cyanate and an alcohol at an elevated temperature (between 80° C. and 200° C.), to produce a urethane carbonic acid. The metal cyanate is placed in an aprotic, polar, organic solvent to form a solution and the alcohol and halogenated carboxylic acid ester are then added to this solution in a continuous manner. The desired amino acid is then produced in a high yield by acidic saponification of the urethane carbonic acid.

One preferred embodiment involves the use of halogenated carboxylic acid esters having the structure of formula (I),

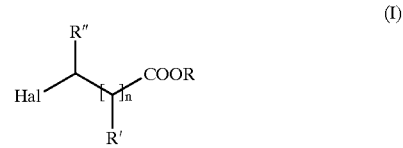

(I)

in which:
n is a whole number from 0 to 10,
R is a $(C_1-C_8)$alkyl,
R' and R" are each independently selected from: H; $(C_1-C_8)$alkyl; $(C_3-C_8)$cycloalkyl; $(C_6-C_{18})$aryl; $(C_7-C_{19})$aralkyl; $(C_3-C_{18})$heteroaryl; $(C_4-C_{19})$heteroaralkyl; $((C_1-C_8)$alkyl$)_{1-3}$-$(C_3-C_8)$cycloalkyl; $((C_1-C_8)$alkyl$)_{1-3}$-$(C_6-C_{18})$aryl; $((C_1-C_8)$alkyl$)_{1-3}$-$(C_3-C_{18})$heteroaryl; Hal signifies chlorine or bromine.

A second preferred embodiment involves the use of halogenated dicarboxylic acid diesters of general formula (II),

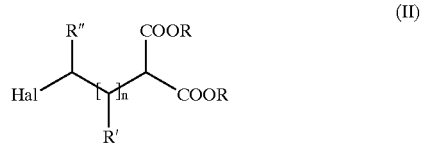

(II)

in which
n is a whole number from 0 to 10,
R is a $(C_1-C_8)$alkyl,
R' and R" are each independently selected from: H; $(C_1-C_8)$alkyl; $(C_1-C_8)$acyl, $(C_3-C_8)$cycloalkyl; $(C_6-C_{18})$aryl; $(C_7-C_{19})$aralkyl; $(C_3-C_{18})$heteroaryl; $(C_4-C_{19})$ heteroaralkyl; $((C_1-C_8)alkyl)_{1-3}-(C_3-C_8)cycloalkyl$; $((C_1-C_8)alkyl)_{1-3}-(C_6-C_{18})aryl$; $((C_1-C_8)alkyl)_{1-3}-(C_3-C_{18})heteroaryl$;
and Hal is chlorine or bromine.

The method of the invention is used with special preference for the production of ω-amino carboxylic acids such as, e.g., ω-aminooctanoic acid. In principle, any cyanate known in the art can be used in reactions. However, the most favored selections will be determined based upon convertibility, purchase price and potential for danger. Alkali cyanates, and particularly metal cyanates are preferably used. The most preferred are lithium-, sodium- or potassium cyanate.

The alcohol used in the reaction should be the most economical available but should permit the formation of urethane in an efficient manner. The use of linear or branched alkyl alcohols such as, eg., methanol, ethanol, propanol, isopropanol, butanol, sec-butanol, isobutanol, tert.-butanol, etc. will be generally preferred.

The solvent used in the formation of urethane should be an aprotic, polar, organic solvent. It should have sufficient solubility for the reaction partners and exhibit inert behavior under reaction conditions. Examples of suitable solvents include dimethylformamide, dimethylsulfoxide, methylpyrrolidone and acetonitrile. Dimethylformamide is particularly preferred.

The temperature during the formation of urethane should be selected so that the reaction takes place rapidly but the formation of byproducts is suppressed as much as possible in order to assure an optimal space/time yield. A suitable temperature for reactions can be determined by routine experiments. In general, the addition of the alcohol and of the halogenated carboxylic acid ester will be carried out at 80° C. to 200° C., preferably at 120° C. to 160° C. and more preferably at about 140° C.

The molar ratio of the individual reactants to each other should be at least 1:1:1 for the halogenated carboxylic acid ester, the alcohol and the metal cyanate. However, ratios can be varied to optimize yield, reaction time and cost. The use of an excess of alcohol and, if necessary, metal cyanate in the range of 1:1–2:1–1.5 relative to the halogenated carboxylic acid ester is advantageous. The use of an excess of alcohol of 10–50 molar % at a ratio of halogenated carboxylic acid ester to metal cyanate of 1:1 is especially preferred.

The urethane carbonic acid formed is saponified to produce the desired amino acid. For compounds of general formula (I), the saponification of the ester and of the urethane, as well as the decarboxylation of the resulting carbamic acid function, take place in parallel. For compounds of general formula (II), a further saponification and decarboxylation of the malonic ester takes place. The reaction can be readily followed based upon the amount of gas being released using methods well known in the art. The acidic saponification is preferably carried out with an aqueous solution of a mineral acid. The use of aqueous hydrochloric acid is especially preferred since the hydrochlorides of the amino acids produced can be readily obtained in pure form as salts by crystallization.

It appears to be important for achieving a high space/time yield to observe the sequence of reactant addition and the reaction conditions described above. Thus, the alcohol should be continuously added together with the halogenated carboxylic acid ester at an elevated temperature to the metal cyanate solution. The continuous addition assures that the reaction partners, alcohol and halogenated carboxylic acid ester, are present in a deficit during almost the entire reaction time. This has a positive influence on the rapidity and yield of product formation (in the case of ω-amino octanoic acid 80% within 3 hours reaction time).

DETAILED DESCRIPTION OF THE INVENTION

The present invention is concerned with the conversion of halogenated carboxylic acid esters to urethane by N alkylation. An alkali metal cyanate is placed in a polar, aprotic solvent, preferably with a relatively high boiling point, and is heated to reaction temperature. Lithium-, sodium- or potassium cyanate can be used as alkali metal cyanates, with potassium cyanate being preferred. Suitable solvents are, in particular, dimethylformamide, dimethylsulfoxide and methylpyrrolidone, with dimethylformamide being preferred. The reaction should generally be carried out at a temperature of greater than 80° C., and more desirably, at a temperature of greater than 140° C.

After the metal cyanate is heated, a mixture of halogenated carboxylic acid ester and alcohol is continuously charged while maintaining the reaction temperature until the complete conversion of the halogenated carboxylic acid ester has taken place. In contrast to many reactions described in the literature, an excess of metal cyanate is not needed and, as a result, less waste salt accumulates. The charging of alcohol and alkylation agent takes place during the entire reaction time, preferably in a time span of 0.5 to 4 hours and advantageously within 1.5 hours.

A quantitative conversion to urethane is achieved, e.g., in the reaction of potassium cyanate with 8-chlorooctanoic acid ethyl ester and ethanol in dimethylformamide, after 4 hours. This effect was not predictable and represents a distinct improvement over other methods involving the use of chlorine-substituted carboxylic acid esters. An additional advantage of the method of the invention is the fact that it can also be used for longer-chain ω-chlorocarbomic acid esters.

In an especially advantageous embodiment, (6-chlorohexyl)malonic acid diesters are reacted with metal cyanate and alcohol to form the corresponding urethane. This process has the advantage that three hydrolyses and two decarboxylations take place in the following reaction of the 6-((alkoxycarbonyl)amino)hexylmalonic acid esters with aqueous hydrochloric acid in a single reaction step. As a result, a large number of purification and isolation steps are avoided. Thus, the method is especially well suited for large-scale use.

Metal chloride salt (e.g., potassium chloride) accumulating during the reaction is separated off by filtration. The solvent used is separated from the product by distillation and can be reused in the reaction. Urethanes formed can be used in raw form or after purification by distillation. In so far as a recycling of the organic solvent can be eliminated, the saponification can be performed even without a previous separation of the organic solvent by distillation.

The hydrolysis of the urethanes produced by alkylation may be performed by placing the reactants in a receiver, without solvent if possible, and heating them to a reaction temperature of approximately 30–120° C. Then acid, e.g., aqueous hydrochloric acid, is charged and the reaction mixture heated further to 100° C. The aqueous hydrochloric acid should typically be in a 4 to 8-fold excess and in a concentration of 10–37%. In general, about a 6-fold excess and a concentration of 15–20% is preferred. The charging of the hydrochloric acid takes place over a period of 0.5 to 3 hours, and, advantageously, within 1.5 hours. During the hydrolysis, the urethane and the ester group are split in one step. Carbon dioxide is produced as waste gas and may be used to follow the reaction. After complete conversion, the water present is spun out, e.g., with the aid of an entraining agent, during which excess hydrochloric acid is also removed. Suitable entraining agents include cyclohexane, ethylcyclohexane and toluene, with cyclohexane being preferred. During the spinning out of the water, the product precipitates as a solid. The isolation of the product takes place by filtration and a subsequent wash. Alternatively, the amino acid can be isolated from aqueous solution ion-exchange methods well known in the art.

If a (6-chlorohexyl)malonic acid diester is reacted to urethane, the non-decarboxylated (6-amino hexyl)malonic acid is obtained after hydrolysis, spinning out of water and separation of the entraining agent. When this compound is heated in substance or in a high-boiling solvent to above 130–150° C., the desired 8-amino octanoic acid hydrochloride precipitates as a solid after another decarboxylation.

In contrast to many methods described in the art, the hydrolysis of the urethanes as described herein takes place without the addition of formic acid. In the case of the production of ω-amino carboxylic acids, complete conversion is achieved after only 3 hours. In the case of carboxylic acids substituted by chlorine, the method permits an exchange of chlorine atoms by a group carrying nitrogen in a surprisingly simple manner, and in a time frame and yield acceptable for a large-scale process.

It should be recognized that even racemates of chiral amino acids can be obtained with the method in as far as a stereocenter is reconstructed by the reaction. The racemate can then be split into the individual enantiomers in a manner well known in the art.

Definitions

Methyl, ethyl, propyl, isopropyl, butyl, isobutyl, sec-butyl, tert-butyl, pentyl, hexyl, heptyl or octyl plus all bond isomers are to be regarded as $(C_1-C_8)$alkyl. The groups can be simply or multiply substituted with heteroatoms such as N, P, S, O or uninterrupted.

An aromatic group with 6 to 18 C atoms is to be understood under the term "a $(C_6-C_{18})$aryl group." This includes, in particular, compounds such as phenyl-, naphthyl-, anthryl-, phenanthryl- and biphenyl groups. The aromatics can be simply or multiply substituted with $(C_1-C_8)$alkoxy, $(C_1-C_8)$haloalkyl, OH, Cl, $NH_2$, $NO_2$. Moreover, they can comprise one or more heteroatoms such as N, O, S.

$(C_1-C_8)$alkoxy is a $(C_1-C_8)$alkyl group bound via an oxygen atom to the contemplated molecule.

A $(C_7-C_{19})$aralkyl group is defined as a $(C_6-C_{18})$aryl group bound via a $(C_1-C_8)$alkyl group to the molecule.

$(C_1-C_8)$haloalkyl is a $(C_1-C_8)$alkyl group substituted by one or more halogen atoms. Chlorine, fluorine and bromine are examples of halogen atoms that may be used.

A $(C_3-C_{18})$heteroaryl group is defined as a five-, six- or seven-member aromatic ring system of 3 to 18 C atoms that comprises heteroatoms such as, e.g., nitrogen, oxygen or sulfur in the ring. In particular, groups such as 1-, 2-, 3-furyl, 1-, 2-, 3-pyrolyl, 1-, 2-, 3-thienyl, 2-, 3-, 4-pyridyl, 2-, 3-, 4-, 5-, 6-, 7-indolyl, 3-, 4-, 5-pyrazolyl, 2-, 4-, 5-imidazolyl, acridinyl, chinolinyl, phenanthridinyl, 2-, 4-, 5-, 6-pyrimidinyl are suitable heteroaromatics. They can be simply or multiply substituted with $(C_1-C_8)$alkoxy, $(C_1-C_8)$haloalkyl, OH, halogen, $NH_2$, $NO_2$, SH, or S—$(C_1-C_8)$alkyl.

A $(C_4-C_{19})$heteroaralkyl denotes a heteroaromatic system corresponding to the $(C_7-C_{19})$aralkyl group.

$(C_3-C_8)$cycloalkyl denotes cyclopropyl, cyclobutyl, cyclopentyl, cyclohexyl or cycloheptyl or cyclooctyl groups.

Halogen is defined as fluorine, chlorine, bromine, iodine.

The chemical structures presented refer to all possible stereoisomers that can be achieved by altering the configuration of the individual chiral centers, axes or planes. Thus, the structures include all possible diastereomers as well as all optical isomers (enantiomers).

EXAMPLES 1.5 moles of potassium cyanate are placed in 750 ml dimethylformamide and heated to 140° C. Then, a mixture of 1.5 moles of 8-chlorooctanoic acid ethyl ester and 1.65 moles ethanol are charged in over a period of 1 hour. The mixture is agitated 3 more hours at 140° C., until conversion is complete. The precipitated potassium chloride is filtered off and excess dimethylformamide is removed on a rotary evaporator under vacuum. The raw product obtained in this manner is placed in a receiver at 100° C. without further cleaning and without solvent. Then, a mixture of 887 g of concentrated HCl and 162 g water is charged over a period of 1.5 hours. After complete conversion (approximately 3 hours), cyclohexane is added, water spun out and the precipitated solid filtered off. After multiple washings and dryings of the product in a vacuum, the hydrochloride of 8-amino octanoic acid is obtained as a white, crystalline solid (melting point:141–144° C.) with 80% yield.

All references cited herein are fully incorporated by reference. Having now fully described the invention, it will be understood by those of skill in the art that the invention may be performed within a wide and equivalent range conditions, parameters and the like, without affecting the spirit or scope of the invention or any embodiment thereof.

What is claimed is:

1. A method of producing an amino acid, comprising:
   a) reacting a halogenated carboxylic acid ester with a metal cyanate and an alcohol at a temperature of between 80° C. and 200° C., to produce a urethane carbonic acid, wherein:
      i) said metal cyanate is placed in an aprotic, polar, organic solvent to form a solution;
      ii) said alcohol and halogenated carboxylic acid ester are added to said solution in a continuous manner; and
   b) producing said amino acid by acidic saponification of said urethane carbonic acid,
   wherein said halogenated carboxylic acid ester is a dicarboxylic acid diester with the structure of formula (II)

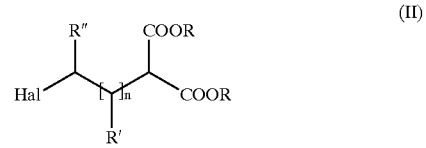

(II)

wherein:
n is a whole number from 0 to 10,
R is a $(C_1-C_8)$ alkyl,
R' and R" are each independently selected from: H; $(C_1-C_8)$ alkyl; $(C_1-C_8)$ acyl, $(C_3-C_8)$ cycloalkyl; $(C_6-C_{18})$ aryl; $(C_7-C_{19})$ aralkyl; $(C_3-C_{18})$ heteroaryl; $(C_4-C_{19})$ heteroaralkyl; $((C_1-C_8)$ alkyl$)_{1-3}$-$(C_3-C_8)$ cycloalkyl; $((C_1-C_8)$ alkyl$)_{1-3}$-$(C_6-C_{18})$ aryl; and $((C_1-C_8)$ alkyl$)_{1-3}$-$(C_3-C_{18})$ heteroaryl; and
Hal signifies chlorine or bromine.

2. The method of claim 1, wherein said amino acid is a ω-amino acid.

3. The method of claim 1, wherein said metal cyanate is a lithium-, sodium- or potassium cyanate.

4. The method of claim 1, wherein said alcohol is an alkyl alcohol.

5. The method of claim 4, wherein said alcohol is methanol or ethanol.

6. The method of claim 1, wherein said aprotic, polar, organic solvent is selected from the group consisting of: dimethylformamide; dimethylsulfoxide; methylpyrrolidone; and acetonitrile.

7. The method of claim 1, wherein the reaction of step a) is carried out at a temperature of between 120° C. and 160° C.

8. The method of claim 1, wherein the acidic saponification of said urethane carbonic acid is carried out with an aqueous solution of a mineral acid.

9. The method of claim 1, wherein said halogenated carboxylic acid ester, said alcohol and said metal cyanate are used in a ratio of: 1 mole of halogenated carboxylic acid ester, to between 1 and 2 moles of alcohol, to between 1 and 1.5 moles of metal cyanate.

10. A method of producing an amino acid, comprising:
a) reacting a halogenated carboxylic acid ester with a metal cyanate and an alcohol at a temperature of between 80° C. and 200° C., to produce a urethane carbonic acid, wherein:
  i) said metal cyanate is placed in an aprotic, polar, organic solvent to form a solution;
  ii) said alcohol and halogenated carboxylic acid ester are added to said solution in a continuous manner; and
b) producing said amino acid by acidic saponification of said urethane carbonic acid;
wherein said halogenated carboxylic acid ester has the structure of formula (I):

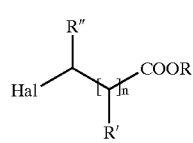

(I)

wherein:
n is a whole number from 0 to 10,
R is a $(C_1–C_8)$ alkyl,
R' and R" are each independently selected from: H; $(C_1–C_8)$ alkyl; $(C_3–C_8)$ cycloalkyl; $(C_6–C_{18})$ aryl; $(C_7–C_{19})$ aralkyl; $(C_3–C_{18})$ heteroaryl; $(C_4–C_{19})$ heteroaralkyl; $((C_1–C_8)\text{alkyl})_{1-3}$-cycloalkyl; $((C_1–C_8) \text{alkyl})_{1-3}$-$(C_6–C_{18})$aryl; and $((C_1–C_8) \text{alkyl})_{1-3}$-$(C_3–C_{18})$ heteroaryl; and
Hal signifies chlorine or bromine;
with the proviso that when R' is hydrogen and R" is hydrogen, n is 1 or 5–10; and with the further proviso that when R" is a $(C_1–C_8)$ alkyl, then n is a whole number from 1 to 10.

11. The method of claim 10, wherein said amino acid is a ω-amino acid.

12. The method of claim 10, wherein said metal cyanate is a lithium-, sodium- or potassium cyanate.

13. The method of claim 10, wherein said alcohol is an alkyl alcohol.

14. The method of claim 13, wherein said alcohol is methanol or ethanol.

15. The method of claim 10, wherein said aprotic, polar, organic solvent is selected from the group consisting of: dimethylformamide; dimethylsulfoxide; methylpyrrolidone; and acetonitrile.

16. The method of claim 10, wherein the reaction of step a) is carried out at a temperature of between 120° C. and 160° C.

17. The method of claim 10, wherein the acidic saponification of said urethane carbonic acid is carried out with an aqueous solution of a mineral acid.

18. The method of claim 10, wherein said halogenated carboxylic acid ester, said alcohol and said metal cyanate are used in a ratio of: 1 mole of halogenated carboxylic acid ester, to between 1 and 2 moles of alcohol, to between 1 and 1.5 moles of metal cyanate.

* * * * *